US009545455B2

(12) United States Patent
Muniyappa

(10) Patent No.: US 9,545,455 B2
(45) Date of Patent: Jan. 17, 2017

(54) DEVICE AND METHOD FOR THE DIAGNOSIS OF GASTROINTESTINAL ALLERGY

(76) Inventor: Pravin K. Muniyappa, Chicago, IL (US)

( * ) Notice: Subject to any disclaimer, the term of this patent is extended or adjusted under 35 U.S.C. 154(b) by 771 days.

(21) Appl. No.: 12/770,418

(22) Filed: Apr. 29, 2010

(65) Prior Publication Data

US 2010/0278753 A1    Nov. 4, 2010

Related U.S. Application Data

(60) Provisional application No. 61/173,681, filed on Apr. 29, 2009.

(51) Int. Cl.
| | |
|---|---|
| *A61B 8/00* | (2006.01) |
| *A61K 49/00* | (2006.01) |
| *A61B 1/31* | (2006.01) |
| *A61M 37/00* | (2006.01) |

(52) U.S. Cl.
CPC ............ *A61K 49/0004* (2013.01); *A61B 1/31* (2013.01); *A61M 37/00* (2013.01); *A61M 2210/1042* (2013.01)

(58) Field of Classification Search
CPC ............ A61B 1/31; A61B 5/14; A61B 5/411; A61B 1/00103; A61B 1/00105; A61B 1/00112; A61B 1/00131
USPC ....................................... 424/9.81, 9.82, 448
See application file for complete search history.

(56) References Cited

U.S. PATENT DOCUMENTS

| | | | | |
|---|---|---|---|---|
| 5,614,167 | A | * | 3/1997 | Hansen et al. ................. 424/9.2 |
| 5,983,899 | A | * | 11/1999 | Hallgren ....................... 128/898 |
| 2003/0165512 | A1 | * | 9/2003 | Wheeler et al. ........... 424/184.1 |
| 2003/0191430 | A1 | * | 10/2003 | D'Andrea et al. .............. 604/66 |
| 2003/0235512 | A1 | | 12/2003 | Carpenter et al. |
| 2006/0115499 | A1 | * | 6/2006 | Brimnes et al. ........... 424/275.1 |
| 2007/0038181 | A1 | | 2/2007 | Melamud et al. |
| 2007/0249661 | A1 | * | 10/2007 | Chen et al. .................... 514/303 |
| 2008/0269635 | A1 | | 10/2008 | Mir et al. |

OTHER PUBLICATIONS

Molinari J A, Allergic Reactions: Increased Immunocological Problem for Healthcare Providers and Pateints, 1998, Journal of California Dental Association.*
Bischoff, et al., "Colonoscopic allergen provocation (COLAP): a new diagnostic approach for gastrointestinal food allergy", Gut, 1997, 40(6): p. 745-753, Published in: Germany.
Lin, et al., "Local Allergic reaction in food-hypersensitive adults despite a lack of systemic food-specific IgE", J Allergy Clin Immunol, 2002, 109(5) pp. 879-887, Published in: Sweden.

* cited by examiner

*Primary Examiner* — Micah-Paul Young
(74) *Attorney, Agent, or Firm* — Factor Intellectual Property Law Group, Ltd.

(57) ABSTRACT

A method and device for the diagnosis of gastrointestinal allergy. The method and the device expose a surface to at least one antigen at a fixed depth. The device includes an application point each having an antigen allowing for the application of the antigen to the surface at a fixed depth. The device may include multiple applications points each with an antigen for simultaneously applying the antigens to the surface.

10 Claims, 2 Drawing Sheets

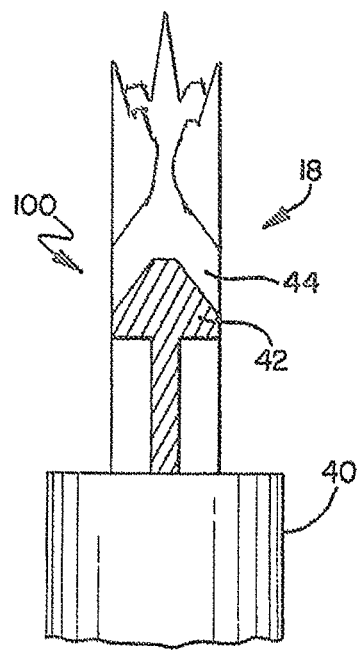
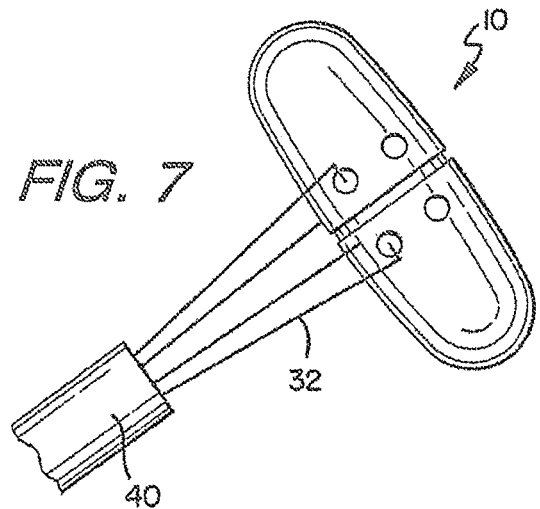
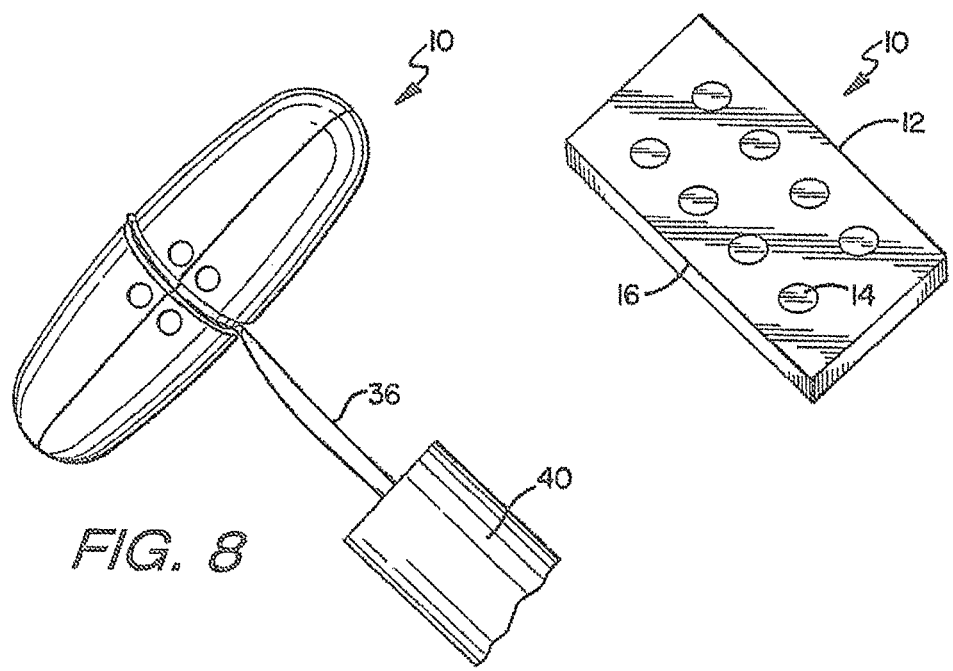

DEVICE AND METHOD FOR THE DIAGNOSIS OF GASTROINTESTINAL ALLERGY

RELATED APPLICATIONS

This application claims priority to U.S. Provisional Application No. 61/173,681 filed on Apr. 29, 2009, the entirety of which is incorporated herein by reference.

FIELD OF INVENTION

The present invention relates generally to the diagnosis of gastrointestinal allergy/immune dysfunction and a method to aid in the diagnosis of gastrointestinal allergy/immune dysfunction.

BACKGROUND OF THE INVENTION

Many allergic reactions involve the interaction of an antigen, also known as an allergen, with an antigen-specific-IgE antibody, also known as an allergen-specific-IgE antibody, and the consequent sequence of events. For a patient to be definitively diagnosed with a particular allergy, two expectations must be met.

First, the patient must have a clinically relevant scenario. That is, upon exposure to an antigen, the patient must have an appropriate allergic response, with the appropriate time interval, and clinical picture.

Second, the patient must demonstrate objective testing consistent with an allergic reaction. In other terms a mast cell is central to allergy. Mast cell distribution is known to be varied among organ systems, and the interaction of antigen with antigen-specific-IgE will cause mast cell degranulation, with the release of mediators, including, but not limited to, histamine, and heparin.

This process of antigen interaction with antigen-specific-IgE causes the major symptoms of allergy which vary by organ system.

In the upper airway, nasal, and sinus area, patients experience nasal and/or eye itching, nose and/or sinus congestion, rhinorrhea, post-nasal drip, sneezing, and/or itching. In the lower airway and lung area—patients experience shortness of breath, wheezing, chest tightness, and/or coughing.

In the skin, patients experience itching, redness, hives (i.e., urticaria), and/or swelling (i.e., angioedema).

In the cardiovascular system, patients experience hypotension, light-headedness, and/or syncope.

Allergic reactions can involve multiple organ systems and lead to any combination of the above symptoms. Alternatively, allergic reactions can also occur in an isolated organ system with symptoms limited to the specific organ system involved.

For making a diagnosis of an allergy, the first requirement is a scenario consistent with allergic disease. This is obtained through a thorough patient history.

The second component of an allergic diagnosis, objective testing for the allergy, is conventionally done via two methods. One method is an in vivo qualitative assay, and the other an in vitro quantitative assay. Both methods are unique and have their own merits and disadvantages. In addition, both methods test for the presence of specific-IgE-antibody. Antibody detection is required to make a definitive diagnosis of an allergy.

As previously mentioned, the first method of objective allergy testing is the in vivo qualitative method of specific-IgE detection. This method is allergy skin testing. Allergy skin testing involves the introduction of antigen into the skin to evaluate for mast cell activation. Mast cell activation is objectively observed in the skin as a wheal and flare reaction. The skin becomes raised and red (the wheal and flare), and this indicates the presence of allergen-specific-IgE. Controls are used during the test as well. A positive histamine control is used, and all patients should have a positive reaction to histamine. If a patient does not react to the control, the failure may be due to medications which blunt the effects of histamine (for example anti-histamines). A negative control of normal saline is used as well. The result from the saline should be negative, without reaction in all patients. However, it may be positive due to low mast cell stability or due to skin irritation. Both controls should be appropriate before the skin tests can be interpreted. This test is typically done on the forearm or the back. The results are visible at 20 to 30 minutes after antigen placement. The presence of antigen-specific-IgE does not make a definitive diagnosis of an allergy unless a clinical scenario consistent with an allergy is present.

On the other hand, RadioAllergoSorbent Test (RAST) testing is an in vitro quantitative method of specific-IgE detection. This is a laboratory based blood test which gives a quantitative measure of specific-IgE. Currently most in vitro quantitative allergy testing is done via an enzyme-linked immunosorbent assay (ELISA). The term "RAST testing" is used to refer to any method of quantitative in vitro specific-IgE antibody detection.

Both testing methods carry caveats and should be interpreted in the proper clinical light. In both testing methods, both the negative and positive controls must be adequate when interpreting skin test results.

In addition, the presence of specific-IgE does not mean that a patient is allergic to the allergen tested. For example, if a patient demonstrated the presence of Cat-specific-IgE on skin testing or RAST testing he is not necessarily allergic to cats. If in the presence of a cat he is symptom free—that is, he has no allergic symptoms—this patient is not allergic to cats. This is a "false positive" result which may be seen in all current testing methods. These "false positive" results indicate the importance of clinical interpretation of test results. That is for a definitive diagnosis of specific allergy to be made, the patient needs both positive testing as well as a history consistent with allergy.

In addition, the lack of detectable specific IgE does not definitively rule out an allergy. For example, a patient who has anaphylaxis, a life threatening allergic reaction to a honeybee sting, may have undetectable Honeybee-specific-IgE. This particular patient may be so sensitive to honeybee, that the undetectable level of IgE is enough to cause a life threatening reaction. Current testing methods are believed to have sensitivity and specificity which is 80%-95%, and clinical correlation is essential in determining a patient's allergic status.

There is a common assumption that specific IgE can be detected in the skin (in vivo) or blood (in vitro) regardless of the organ system (e.g., skin, gut, upper airway, lower airway, etc) which is affected by allergy. This assumption has been proven to be false. Lin et al., describes this in the following reference: Lin, X. P., et al., *Local allergic reaction in food-hypersensitive adults despite a lack of systemic food-specific IgE*. J Allergy Clin Immunol, 2002. 109(5): p. 879-87.

For example, five patients have five different allergic manifestations after eating a peanut. Patient 1 has isolated hives only. Patient 2 has isolated airway symptoms. Patient 3 has isolated hypotension, light-headedness and syncope.

Patient 4 has only abdominal pain, and abdominal bloating. Patient 5 has all of the above symptoms. All of these five patients have allergic manifestations after eating a peanut, and all of them should avoid peanuts.

It is important to make a definitive diagnosis of an allergy, because the avoidance of the allergens can be very difficult. If skin or RAST testing for a specific-IgE is positive, this is an easy method to correlate to the history. In the case of positive testing and a strong history, a definitive diagnosis can be easily made. However, there are many patients in whom the specific-IgE cannot be detected via skin and RAST testing. This is especially true of patients with isolated gastrointestinal symptoms. Again, for a definitive diagnosis of allergy to be made: objective testing must be positive and the history must be consistent with allergy. The diagnosis of gastrointestinal allergy is difficult in patients with a mild to strong clinical history of allergy and negative skin and RAST testing. This is a problem because the negative skin and blood testing may not be truly reflective of the presence or lack thereof of antigen-specific-IgE within the gastrointestinal mucosa.

Gastrointestinal Allergy

There are many patients, with negative skin allergy testing and negative RAST testing, who feel their gastrointestinal symptoms are due to ingested antigens. It is difficult to make a diagnosis in these patients due to a lack of appropriate diagnostic modalities.

Patients with gastrointestinal allergy may have a wide variety of symptoms including, but not limited to: nausea, diarrhea, abdominal pain, flatulence, cramps, obstipation, constipation, and/or vomiting. Most patients are able to relate symptoms and worsening symptom severity to specific antigen intake. But without a diagnostic test a definitive diagnosis of allergy cannot be proven or ruled out. Patients may suggest multiple suspected allergic triggers for their gastrointestinal symptoms. However, a definitive diagnosis of gastrointestinal allergy must be made to avoid extreme lifestyle alterations which may include extreme efforts to avoid perceived allergy triggers.

The problem of diagnosing suspected isolated gastrointestinal allergy in patients with negative testing for antigen-specific-IgE is that objective testing is lacking for many patients. That is their clinical symptoms are mild to strongly suggestive of allergy, but their objective testing both via blood (RAST) and via skin testing is negative.

It has been shown that there can be organ specific, local production of specific allergic antibodies in such patients, and this can be a key factor in symptom creation. The current standard is to try to reproduce the gastrointestinal symptoms via a double blind placebo controlled food challenge (DBPCFC). But the DBPCFC is quite cumbersome, time consuming, and often non-reproducible. Consequently, it is not done by most physicians.

Colonoscopic Allergen Provocation (COLAP (1))

In 1997, COLAP was described in German literature, with the following citations: Bischoff, S. C., et al., *Clinical significance of the colonoscopic allergen provocation test.* Int Arch Allergy Immunol, 1997. 113(1-3): p. 348-51; and, Bischoff, S. C., et al., *Colonoscopic allergen provocation (COLAP): a new diagnostic approach for gastrointestinal food allergy.* Gut, 1997. 40(6): p. 745-53.

The Colonoscopic allergen provocation test (COLAP) is a specific allergy testing within the gastrointestinal tract. In the cecal portion of the colon, allergens are applied with a straight needle. The testing is very effective and clinically useful, especially in those patients who have a history consistent with allergic gastrointestinal disease, but with negative skin testing and RAST testing. This test as described by Bischoff does have many advantages, but there disadvantages as well. The literature does show the effectiveness of local gastrointestinal mucosal testing for isolated gastrointestinal symptoms thought to be related to allergy, but with negative objective skin testing and negative in vitro testing.

There are several positive aspects to local testing in the gastrointestinal mucosa. Specifically, 45% of antigens tested induced a positive reaction in the cecum, but not on the skin or via RAST. This type of testing can aid in gaining a definitive diagnosis in almost 77% of cases of suspected gastrointestinal allergy. In addition, results of the COLAP testing were visible within 20 minutes.

There are, however, several negative aspects of the COLAP testing described by Bischoff. The testing involved a colonoscopy and testing in the cecum of the colon. A straight needle was introduced via the endoscope into the cecum, and antigen was introduced. The mucosa of the cecum was then pricked (broken) via the needle, and the results were visually measured 20 minutes later. The technique itself is quite cumbersome and time consuming. The testing must be done one antigen at a time—antigen, by antigen, including controls. This prolongs the colonoscopy, and is often unacceptable depending on the number of antigens tested. Further, the cecum is a distant location, and a large amount antigen is used to fill the endoscope. This raises the cost of this type of testing. The most serious risk of COLAP testing involves a significant risk of gastrointestinal perforation. The mucosa of the cecum is the thinnest of the colon, and there is a significant risk of perforation, while using a straight needle to break or prick the mucosa. This is especially true because patients are not sedated for this procedure. They are under conscious sedation, and are still able to move. Movement increases the likelihood of perforation with a straight needle. The needle is also reused for each antigen, and flushed out in between uses. There is a risk of cross-contamination from previous antigens, which may cause false positive test results.

Because of the risk, cost, and cumbersome nature of this testing, it is not currently done anywhere on humans. Also it is not consistently reproducible because the amount of antigen used varies and the depth of penetration of the needle into the colonic mucosa varies. In sum, because of the negative aspects of the technique, colonoscopic allergen provocation is not done.

SUMMARY OF THE INVENTION

The present invention provides both a method and a device to aid in the diagnosis of gastrointestinal allergy in patients with suspected gastrointestinal allergy. As used herein, "gastrointestinal allergy" and "immune dysfunction" may be used interchangeably. In general, the method is to apply a single antigen or multiple antigens locally into the colonic mucosa with a standardized efficient technique and the device allows this to be done. Preferably, the present invention delivers antigens to the cecal portion of the colon. However, any portion of the gastrointestinal tract may be used. Ideally, the visual readings are taken every minute for the first 20 to 30 minutes. However, readings may be taken continuously or during any interval of time for up to 1.5 hours.

The method involves scratching the most superficial layers of the colonic mucosa while simultaneously applying commercially available antigens and/or antigens produced by the clinician to a fixed or variable depth. These antigens may include, but are not limited to, wheat, egg, soy, milk, peanut, and the like. Antigens are not limited to foods, and may include any agent capable of inducing an immunologic response. Antigens used for testing may include but are not limited to, aeroallergens, pharmaceuticals, chemicals, and/or metals. Antigens may be customized for specific patients based on their clinical history of suspected gastrointestinal allergy. However, a standard panel may be used, which would include the most common suspected antigens or allergens. As used herein, 'antigen" and 'allergen" are used interchangeably and refer to any agent capable of inducing a local or systemic immune response.

The device and method of the present invention may be used to deliver antigens to any other portion of the colon or any other portion of the gastrointestinal tract. The device and method of the present invention may be used to test immune reactions in any organ/organ system and/or any other type of allergic reaction without departing from the scope of the present invention. Further, in other embodiments, the visual readings may be conducted at any time interval without departing from the scope of the invention.

In an embodiment of the present invention, the invention is a device that is a capsule shaped device which opens to reveal a self contained testing device, which preferably compromises antigen, and a prick device, which is able to penetrate the mucosal surface of the colon. Accordingly, in a preferred embodiment, the capsule is configured in such a fashion as to allow its contents to be exposed to an outside.

Preferably, the device is of a suitable size to enter the gastrointestinal tract. However, the device may be any shape or size suitable for entry into a particular organ/organ system. In other embodiments, the prick device may penetrate the surface of any other part of the gastrointestinal track and/or the surface of any organ/organ system. The surface may be an epithelial surface, a mucosal surface, or the like.

In a preferred embodiment, the device of the present invention is made of plastic. However, the device may be made of any other material/combination of materials such as ceramic, metal, or the like.

As used herein, "device" may refer to "capsule."

In certain embodiments, the device contains a latch to open it, and appropriate holes where a standard tri-prong grasper attaches. A standard tri-prong grasper is able to fit through the ports of the endoscope and is used often in interventional endoscopic gastrointestinal procedures, such as polyp removal. The steps for device deployment, activation, testing, and result reading are detailed.

The capsule shaped device may be lubricated and a loop snare may be inserted through the standard interventional port of the endoscope. The loop snare may be secured around the capsule shaped device via a groove. The device may be inserted in the rectum, and may be followed by the insertion of the endoscope into the rectum by the physician. The endoscope then may be inserted through the sigmoid colon, through the ascending colon, through the transverse colon, and through the descending colon into the cecum. During this process the device may be towed to the cecum as it follows the endoscope.

In the cecal area the device may be released from the loop snare, and the loop snare may be removed. A standard tri-prong grasper may be attached to the device. The tri-prong grasper may be inserted into the colon via the interventional port of the endoscope. When the tri-prong grasper is attached to the capsule device, it may open along the long axis as the latch mechanism is released. Then the plunger attachment device may be attached to the plunger attachment site, and the device may be loaded. Loading of the device describes a process by which the antigen within the device is pushed onto the surface of the prick tips. The viscous antigen stays in place on the prick tips via surface tension. The device may be then applied to the cecal wall. During this process the mucosal surface may be scratched and antigen may be simultaneously applied to the scratched area.

This method and device can be applied to any area of the gastrointestinal tract. In the preferred embodiment, the cecum is preferred because it provides a large area for testing, and demonstrates the least spasming within the colon. However, this method and device can be applied to any area of the gastrointestinal tract. Further, the device may be transported to any section of the gastrointestinal tract by various methods.

Results are recorded every minute for 20 to 30 minutes. The physician may be observing the gastrointestinal mucosa for the presence of erythema, and edema which is indicative of mast cell degranulation or cell activation, which is consistent with an allergy. The observer should notes the results every minute. After satisfaction that results are recorded, the device may be released from the tri-prong grasper. The tri-prong grasper is removed from the colon, and the loop snare may be reinserted into the colon via the interventional port of the endoscope. The loop snare may be used to close the device, and the device may be removed from the cecum as the endoscope is removed from the colon.

The preferred embodiment uses a loop snare and tri-prong grasper, to deploy and activate the device. However, other methods of deployment and activation may be used without departing from the scope of the invention. The preferred embodiment for the device and method utilizes a capsule shaped device. A secondary embodiment is described as a device compromised of a prick tip, a plunger-antigen complex, and a catheter, which is inserted thru the port of the endoscope and can test a more limited number of antigens. Any method of deployment and activation of the device may be used, including Micro-Electro-Mechanical Systems (MEMS).

Another embodiment of the device involves exposing the gastrointestinal mucosa to specific antigens or allergens for a prolonged period time (from 1 hour to 72 hours). The device in the current embodiment is a rectangular patch which contains 8 antigens, including various foods, drugs, and the like. The device is attached to the rectal mucosa with standard endoclips. After the device is removed the mucosa is visually observed after an interval period which varies from 1 hour to 96 hours. A variety of antigens in variable quantities applied over various surface areas and shapes may be used without departing from the scope of this invention. This embodiment may be applied by other methods to the mucosal surface, including but not limited to sutures and adhesives. The backing of the patch may be made of degradable paper, plastic, and polyvinylchloride, or other materials.

The present device and method possess the characteristics which are believed to be needed for an effective and safe device to aid in the diagnosis of gastrointestinal allergy.

The device and method must provide a low risk of perforation. This device does so because the fixed depth of application into the cecal mucosa is fixed by the length of the prick tips or of the application points on the patch. It is important to note that the cecum is the thinnest portion of the colon, and there is a moderate risk of perforation.

The device and method is efficient and rapid. This device may be easily transported to and removed from the cecum.

This device allows for the testing of multiple simultaneous allergens or a single antigen. This device and method may be easily used to apply antigens to the cecal wall and results are quickly available. Thus, the present invention provides an efficient and rapid tool to aid in the diagnosis of gastrointestinal allergy.

The device and method provide results which are reproducible. This is achieved due to minimizing factors which may affect outcome. The two main factors which are standardized by this device and method are the depth of penetration; this is done via the fixed length of the prick tip. The second factor which is standardized is the amount of antigen applied to the mucosa, which is fixed within the device. Standardization of these two factors allows for the reproducibility of results.

The device is easily usable, disposable, and cost effective. Furthermore it provides a high degree of safety and reproducibility.

DESCRIPTION OF THE DRAWINGS

The present invention will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

FIG. 6 is a partial side cut away view of an embodiment of the present invention.

FIG. 7 is a side view of an embodiment of the present invention with an application device.

FIG. 8 is another side view of an embodiment of the present invention with another application device.

FIG. 9 is a top perspective view of a device according to an embodiment of the present invention.

DETAILED DESCRIPTION

Figure 1:
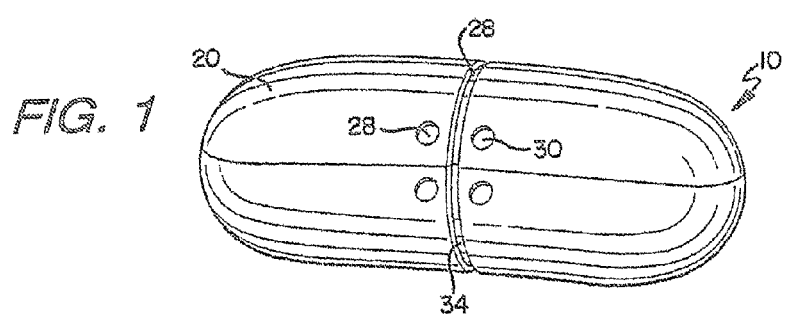
FIG. 1 is a front view of an embodiment of a device according to the present invention.
Figure 2:
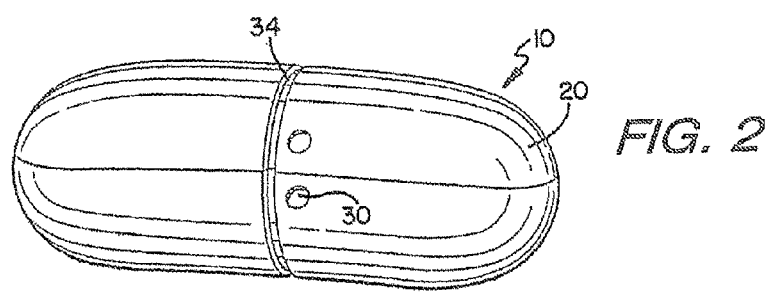
FIG. 2 is a back view of an embodiment of a device according to the present invention.
Figure 3:
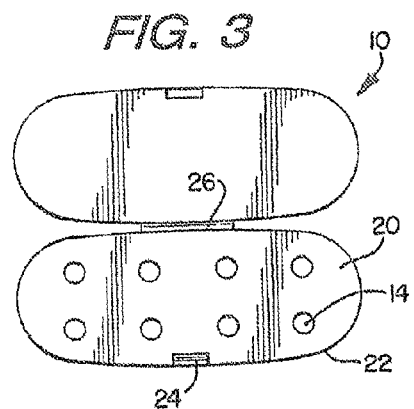
FIG. 3 is a top view of an embodiment of a device according to the present invention.
Figure 4:
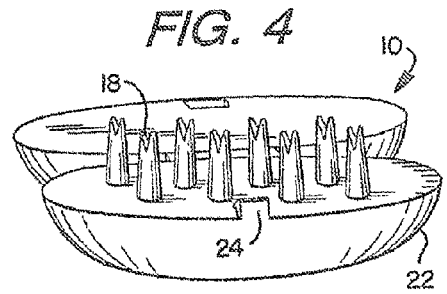
FIG. 4 is a side perspective view of an embodiment of a device according to the present invention.
Figure 5:
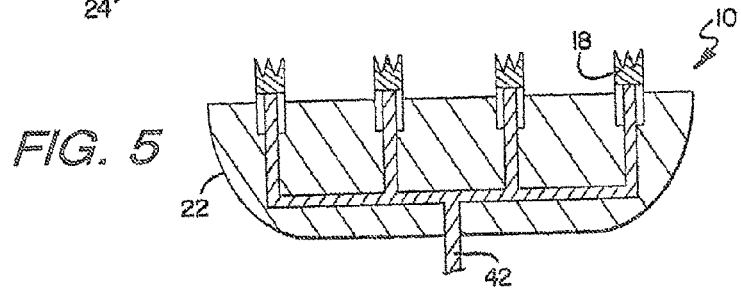
FIG. 5 is a side cut away view of an embodiment of a device according to the present invention.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

In one aspect of the present invention, the invention is a device 10 to apply antigens thru the mucosal surface of the gastrointestinal tract. The device 10 may include a plurality of application points 12. Each application point 12 contains an antigen allowing for the simultaneous application of multiple antigens to a surface. The antigen on each application point 12 is preferably a different antigen allowing for multiple different antigens to be tested simultaneously.

In an embodiment, the device 10 may be a patch 14 with the application points 12 disposed on a backing material 16. The application points 12 on the patch will allow the antigens to be applied to the surface at a fixed depth, i.e., on the top of the surface only.

In another embodiment, the device 10 includes eight (8) application points 12, which will allow for the application of eight (8) different antigens at the same time.

In yet another embodiment, the application points 14 may be a prick-tip 18. The prick-tips 18 have a fixed length relative to a housing 22, such that they will be applied to the surface a fixed depth. In other words, the prick-tip 18 will only penetrate the surface a fixed depth.

The device 10 may be a capsule 20 and the application points 14 are disposed within the housing 22. The housing 22 may include a latch 24 and a hinge 26.

The device may also include grasping means 28. Exemplary grasping means 28 include holes 30 to be grasped by a tri-pronged grasper 32 or a groove 34 to be grasped by a loop snare 36. Those of ordinary skill in the art will appreciate that these devices (tri-pronged grasper 32 and a loop snare 36) can be used with an endoscope 40.

The device 10 may also include a plunger extension 42. The plunger extension 42 moves the antigen 44 from the prick-tip 18 to the surface.

In another embodiment, the device 100 may be a single prick-tip 18 which is individually deployed thru the endoscope 40 and tests antigens individually. The prick-tip 18, unlike a syringe and needle, will only penetrate the surface a fixed distance. This will minimize the chances that the device 100 (or the prick-tip 18) will perforate the colon or tissue.

The present invention also relates to a method to diagnose a gastrointestinal allergy. The method may include the steps of providing a device including a plurality of applications points each application point containing an antigen, exposing a surface to the antigens simultaneously, and, observing the reaction of the surface to the antigens.

The device may be, for example, a patch or a capsule.

The method may also include the step of introducing the device into a bodily cavity. This may be done, for example, by a tri-prong grasper or a loop snare.

The method may further include the step of removing the device from the bodily cavity.

If the device is a capsule, the method may include the step of opening the capsule.

The step of exposing a surface to the antigens simultaneously may further include the step of scratching the surface or penetrating the surface. In addition, penetrating the surface may include penetrating the surface a fixed depth.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the invention is therefore defined by the following claims.

The invention claimed is:

1. A method to diagnose a gastrointestinal allergy comprising the steps of:

providing a device including a plurality of application points each containing an antigen;

introducing the device into a colon;

exposing a surface of the colon to the antigens at a fixed depth by establishing contact between the surface and the plurality of application points; and, observing a reaction of the surface to the antigens, wherein a plurality of different antigens are exposed to the surface at a fixed depth simultaneously and, wherein the surface that is being observed is within the colon when the observing step is being performed.

2. The method of claim 1 wherein the device is a patch.

3. The method of claim 1 wherein the device is a capsule.

4. The method of claim 1 further comprising the step of removing the device from the colon.

5. The method of claim 3 further comprising the step of opening the capsule.

6. The method of claim 3 wherein the step of exposing a surface to the antigen includes the step of scratching the surface.

7. The method of claim 3 wherein the step of exposing a surface to the antigen includes the step of penetrating the surface.

8. The method of claim 1 further comprising the step of taking visual readings of the colon exposed to the antigens periodically up to a total period of 1.5 hours.

9. The method of claim 8 wherein the visual readings of the colon exposed to the antigens are taken every minute for a total period of 20 to 30 minutes.

10. The method of claim 1 wherein the device is introduced to the colon in a cecal portion of the colon.

* * * * *